(12) United States Patent
Kubin et al.

(10) Patent No.: US 7,390,510 B2
(45) Date of Patent: Jun. 24, 2008

(54) PREPARATION OF HYPERICIN BONDED WITH POLY-N-VINYLAMIDES

(75) Inventors: Andreas Kubin, Vienna (AT); Hans Günther Loew, Vienna (AT)

(73) Assignee: Sanochemia Pharmazeutika AG, Vienna (AT)

( * ) Notice: Subject to any disclaimer, the term of this patent is extended or adjusted under 35 U.S.C. 154(b) by 0 days.

(21) Appl. No.: 10/527,016

(22) PCT Filed: May 21, 2001

(86) PCT No.: PCT/AT01/00159

§ 371 (c)(1),
(2), (4) Date: Dec. 21, 2005

(87) PCT Pub. No.: WO01/89576

PCT Pub. Date: Nov. 29, 2001

(65) Prior Publication Data

US 2006/0127349 A1    Jun. 15, 2006

(30) Foreign Application Priority Data

May 23, 2000    (AU) ................................ A 896/2000

(51) Int. Cl.
*A01N 65/00*    (2006.01)
(52) U.S. Cl. ...................................... 424/725
(58) Field of Classification Search ............ None
See application file for complete search history.

(56) References Cited

U.S. PATENT DOCUMENTS

| 5,952,311 | A | | 9/1999 | Kraus et al. ................... 514/44 |
| 6,063,401 | A | * | 5/2000 | Cody ......................... 424/451 |
| 6,472,439 | B1 | | 10/2002 | Schierstedt .............. 514/772.4 |
| 6,890,561 | B1 | | 5/2005 | Blatt et al. .................. 424/490 |
| 2001/0000326 | A1 | * | 4/2001 | Bombardelli et al. ....... 424/730 |
| 2002/0150637 | A1 | * | 10/2002 | Castillo et al. .............. 424/730 |

FOREIGN PATENT DOCUMENTS

| DE | 19756677 | | 6/1999 |
| EP | 0702957 | | 12/1998 |
| JP | 409262279 | * | 10/1997 |
| WO | WO 94/14956 | | 7/1994 |
| WO | WO 00/25824 | | 5/2000 |
| WO | WO 01/07009 | | 2/2001 |

OTHER PUBLICATIONS

Diwu, "Novel therapeutic and diagnostic applications of hypocrellins and hypericins," *Photochemistry and Photobiology*, 61:529-539, 1995.

* cited by examiner

*Primary Examiner*—Michael V Meller
(74) *Attorney, Agent, or Firm*—Fulbright & Jaworski

(57) ABSTRACT

The invention relates to an active agent combination for diagnosing and treating tumours, comprising a water-soluble complex or a water-soluble compound of pure hypericin and a poly-N-vinylamide, especially PVP.

5 Claims, 1 Drawing Sheet

Fig. 1:

Hypericin-PVP-Complex

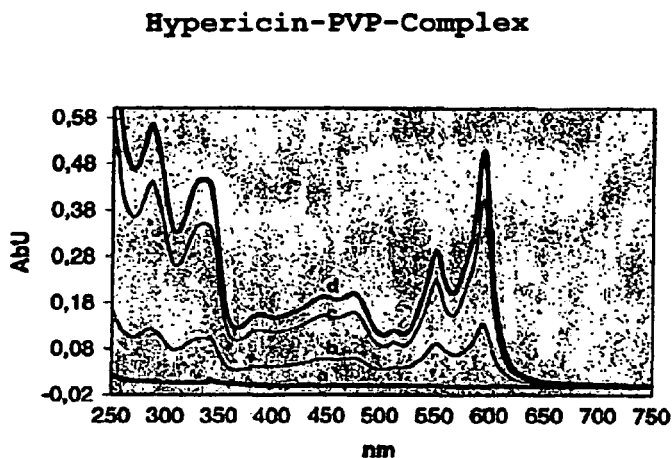

Fig. 2:

Human, erythro-leukaemic K562 cell line, incubated with hypericin-PVP-complex

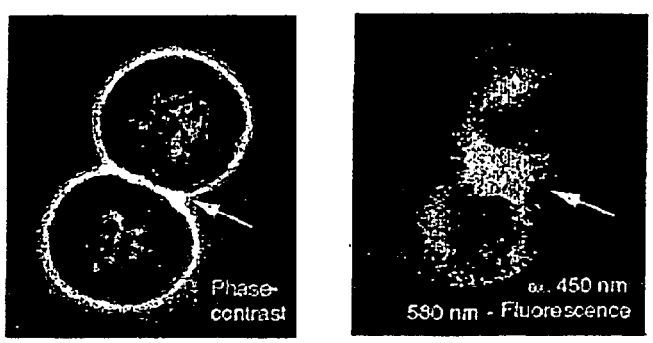

Postmitotic distribution of the sensitizer-complex indicates a high affinity to adhesion contact points of the cells. (>) High postmitotic affinity of the hypericin-complex promotes the photodiagnostic specificity of the substance with regard to proliferating cancer tissue.

PREPARATION OF HYPERICIN BONDED WITH POLY-N-VINYLAMIDES

This application is a national phase application under 35 U.S.C. § 371 of International Application No. PCT/AT01/00159 filed 21 May 2001, which claims priority to Austrian Application No. A 896/2000 filed 23 May 2000. The entire text of each of the above-referenced disclosures is specifically incorporated herein by reference without disclaimer.

Hypericin is often found in nature and is a colorant and plant substance respectively, which is not only contained in *Hypericum perforatum* (St. John's Wort) but also in many other *Hypericum* species (*Hypericum hirsutum, H. montanum* etc.), as well as in different other plants (e.g. in buckwheat with side chains as fagopyrin). This pigment is found further in protozoans (*Blepharisma, Stentor coeruleus*), in "half-wings" (bugs, *Hemiptera*) and as a preliminary stage in agaric *Dermocybe austroveneta*. The lichen species *Nephroma laevigatum* contains hypericin derivatives as well.

Via emodin from *Cortex frangulae* (buckthorn bark) a simple semisynthetic way to hypericin arises.

Since about 20 years hypericin is examined regarding its possible use for therapeutical applications. However the lipidic and water-insoluble characteristics of hypericin make the application in the human body difficult.

EP 0 702 957 B1 and DE 197 56 677 A1 respectively describe drug extracts from different plants, that are narrowed until dry after addition of polyvinylpyrrolidone (a poly-N-vinylamide). Thereby a heterogeneous mixture of some hundreds to thousand different plant substances and polyvinylpyrrolidone (in the following in short referred to as PVP) is generated, that eventually shall be used for peroral taking.

In documents WO 94/14956 and U.S. Pat. No. 5,952,311 B1 hypericin is mixed with an energy dispensing substance like luciferin. This chemical activator substance eventually transfers energy to the photosensitizer.

In the last 25 years the selective photosensitization of malignant tissues or tissue diseases of different kind evolved into an independent medical field [1, 2, 6]. Therein in particular two methods are clinically applied [3]:

utilization of physical effects (e.g. fluorescence induced by light) for diagnosis (photophysical diagnosis, PPD)

utilization of the photodynamic processes induced by light as form of therapy (photodynamic therapy, PDT)

Today the development of PDT and PPD shows a progressive course. Since 1992 the monthly output of scientific publications nearly trebled (Current Contents: Life Sciences). This fact can be ascribed on the one hand thereto, that the PDT has proven to be an effective tumor therapy and which on the other hand is also used for non-malignant diseases like for example vascular, virus diseases.

PDT and PPD use mechanisms, that underlie the interaction between light and tissue. Mediators of this interactions are a suitable photosensitizer and oxygen. Thus four spheres of influence arise—light, sensitizer, oxygen and tissue matrix (physical-optical and chemical nature of tissue [4, 5]), whose combined action enables the successful application of PDT and PPD. Photosensitizers, which exhibit low systemic toxicity and in the ideal case concentrate in malignant tumors are administered. Ensuing exposure with visible light induces photochemical reactions, mainly of type II, but of type I as well, that to a large extent cause a destruction of biomembranes, biomolecules and subcellular organelles [3]. These reactions are therapeutically utilized in the photodynamic tumor therapy, in which cytotoxic reactants of the activated photosensitizers destroy tumor cells. Furthermore sensitizers concentrated in malignant lesions can be established to diagnostic methods via their fluorescence light.

Now in a first aspect the present invention concerns an active agent combination for the diagnostics and treatment of tumors, comprising a water-soluble complex or a water-soluble compound of pure hypericin, as the case may be, and a poly-N-vinylamide. It is known, that poly-N-vinylamides like e.g. PVP complex colorants, surprisingly it turned out in experiments, that lipophilic colorants as well like hypericin can be brought into aqueous solution that way. Especially for the systemic application of larger amounts (up to 5 mg/kg body weight) up to now the appropriate aqueous form of administration was lacking, which is now provided by the active agent combination according to the invention for the first time.

In particular the present invention concerns an active agent combination, comprising a water-soluble complex or a water-soluble compound of pure hypericin, as the case may be, and polyvinylpyrrolidone (PVP) of different degrees of polymerization and cross-linking. By bonding of the pure substance hypericin to polyvinylpyrrolidone (PVP) a well water-soluble complex of the per se water-insoluble sensitizer hypericin can be presented, which is suitable for therapeutic and diagnostic applications. By the complexing of hypericin with PVP a water-soluble form of hypericin is available for the first time, which is easily applicable and with which a better distribution of the sensitizer and a better concentration and selectivity in pathological tissue can be achieved. The use of strongly tissue irritating organic solvents thus becomes avoidable and a physiologically favorable form of application of sensitizers (hypericin, complexed with PVP=colorant complex) for diagnostics or treatment of malignant but also non-malignant diseases presentable.

The water-soluble active agent combination can for example be employed in the execution of photophysical diagnostics (PPD). After selective binding of the complex to lesions of human tissue, the hypericin is stimulated as colorant with e.g. electromagnetic radiation (light) and the physical or chemical response, as the case may be, is utilized for diagnostics. Lesions e.g. in the bladder (by rinsing) could thus be stained and be detected successfully via fluorescent light after stimulation.

The pure substance hypericin can be isolated e.g. from plants or synthetic hypericin, for example synthesized from emodin, can also be employed, bonded or complexed with polyvinylpyrrolidone (PVP) of different degrees of polymerization and cross-linking. Thereby the otherwise water-insoluble colorant hypericin can be administered in aqueous form for different medical purposes. Hypericin is employed in chemical pure form, plant extracts, that are composed of several hundred substances, are not suitable and not object of the present invention. In the state of the art PVP is used as substitute for blood serum, artificial lachrymal fluid, for detoxication and as binding and coating agent for tablets (oral application). As substitute for blood serum however today mainly dextrans, gelatine-starch-derivatives and serum-protein-solutions are used, which can also complex colorants and can be employed as adjuvants in the active agent combination according to the invention. By the use of these different solubilizers the tissue selectivity and affinity is altered as well, thus a more selective concentration in the corresponding tissue is promoted.

Polyvinylpyrrolidones (PVP) with a degree of polymerization of low molar weights (10000-90000 g/mol) are preferably used, since these can diffuse through cell membranes and are excretable. As occasion demands the degree of polymerization of PVP can also be set higher.

According to a preferred embodiment of the present invention the molar ratio of hypericin to poly-N-vinylamide in the active agent combination is about 1:1. In particular depending on the field of application about the following concentrations exist in the water-soluble active agent combination:

hypericin from 1 μmol/l to 0.1 mol/l
poly-N-vinylamide from 1 μmol/l to 0.1 mol/l.

Moreover the molar ratio of PVP to hypericin is dependent on the degree of polymerization and cross-linking of the PVP. The smaller the molar weight of PVP, the higher its concentration in relation to hypericin has to be, in order to completely complex the hypericin as sensitizer. With topical administration the concentration of hypericin has to be set even higher because auf the low diffusion rate.

Further the present invention relates to a process for the production of the active agent combination according to the invention, whereby hypericin is bonded or complexed, as the case may be, with a poly-N-vinylamide, preferably PVP. In doing so the complexing is carried out preferably in aqueous, optionally buffered solution. Thus for example hypericin (isolated from *Hypericum perforatum* or e.g. synthesized from emodin) can be complexed in aqueous solution (for instance physiological salt solution) with polyvinylpyrrolidone (PVP) for formation of the water-soluble active agent combination according to the invention. By the process according to the invention complexes and compounds, as the case may be, are produced, which can be activated, which comprise hypericin, that is complexed or covalently bonded with poly-N-vinylamide of different degrees of polymerization.

Further the active agent combination is preferably provided in a way known per se for the intravenous, intracavitary, inhalative, oral, intraperitoneal and topical administration, in hydrophilic or hydrophobic carriers, preferably in form of a solution, a cream, a gel, an aerosol, of emulsions or as a plaster.

According to a further aspect of the present invention the use of the active agent combination according to the invention for the production of a medicament is provided, in particular for the production of a medicament for the treatment of tumors and diseased tissue. Susceptible to treatment are above all tumors and lesions on and under the skin as well as in cavities and lumens or parts of tissue, which lie deeper. The transport of the active agent combination according to the invention preferably takes place via the vessels or by diffusion through skin and/or tissue to the lesions, where a selective concentration of the active agent combination due to different morphology and physiology for instance of tumors takes place. Non-physiological (pathological) processes in the organism comprise benign as well as malignant diseases. All these diseases are characterized by increased metabolism. Also due to this fact, the active agent combination according to the invention preferably accumulates in these body regions. Thereby an increased sensitization of the diseased tissue area is to be achieved. The light energy (electromagnetic radiation) necessary for stimulation can for instance be brought to the target tissue my means of an optical waveguide. In cavitary regions (cavities like e.g. the bladder as well) the diffusion of the colorant-complex into the lesions can be made possible via rinsing of the tissue also with higher-molecular PVP.

The use of the active agent combination according to the invention for the production of a means of diagnosis for photophysical or photodynamic diagnostics, as the case may be, and for the early cancer diagnosis is preferred as well.

The active agent combination according to the invention concentrates in malignant as well as benign lesions, but not in healthy tissue. Thus the detection of lesions via emitted fluorescent light is possible (diagnostics). The selective sensitization further makes therapeutical treatment (photodynamic therapy) possible.

If with the first treatment with the active agent combination according to the invention the complete removal of malignant or pathological tissue can not be achieved, a repetition of the therapy is possible. If necessary, it is treated thereafter several times at intervals of some weeks.

The active agent combination according to the invention is administered with systemic application about 0, 1 to 36 hours before the treatment or diagnosis, as the case may be. In doing so dosages from 0, 1 mg to 5, 0 mg active agent combination per kg body weight have proven to be favorable. The concentration in the target tissue is determined according to conventional methods (fluorescence spectroscopy).

The complexation of hypericin and PVP is characterized by the special selectivity. According to first examinations by means of confocal laser microscopy the substance concentrates in tumor cells and gets as far as into the endoplasmatic reticulum of the cell, but not into the cell-nucleus (chemical/toxical effects on the genetic information in the cell-nucleus can thus be held behind). The advantages over the studies conducted only sporadically with other sensitizers like porphyrins and their precursors (5-amino-levulinic acid) are:

- besides photo-sensitization of the affected tissue side effects hardly arise: hypericin-PVP is relatively inert for the metabolism,
- short biological half-life of hypericin (34-38 h),
- good water-solubility of the complex, however hypericin itself is lipophilic and can be delivered from the complex into lipid cell compartments,
- from the results so far, an excellent tumor selectivity can be expected, with many therapeutical and diagnostic application possibilities,
- hypericin is a natural plant substance, the raw materials are St. John's Wort, which can be cultivated in Austria (porphyrins are synthetic or from cattle or pig blood, as the case may be).

The present invention is now further elucidated with reference to the accompanying figures.

FIG. 1 shows the time-dependent solubility of hypericin after complexation by PVP. Without PVP no absorption shows in the relevant spectral region (curve a), in aqueous environment hypericin forms at once insoluble aggregates, that precipitate and above all do not show any fluorescence any more (see Diwu Z. et al. [14]). On the other hand the present solution of hypericin-PVP shows the typical absorption spectrum and emits fluorescent light at a wave length of about 600 nm (hypericin+PVP after 30 minutes, curve b; hypericin+PVP after 60 minutes, curve c; hypericin+PVP after 180 minutes, curve d). This shows, that hypericin exists in dissolved form (hypericin in aggregated or microdispersive form does not emit fluorescent light after stimulation).

In FIG. 2 micrographs of human erythro-leukaemic cells of the K562 cell line are shown, which were incubated with the hypericin-PVP-complex according to the invention. The postmitotic distribution of the complex suggests a high affinity to adhesion contact points of the cells (see arrow), whereby the photodiagnostic specificity of the hypericin-PVP-complex according to the invention with regard to proliferating cancer tissue is promoted.

Clinical Examination

The method was tested with four patients with well differentiated bladder tumors. Here the substance (hypericin-PVP-solution) was instilled via a thin bladder catheter. Two hours later a cystoscopy took place with the aid of a fluorescence system (D-Light, Storz, GER). In doing so a blue violet light for stimulation of fluorescence is employed. The fluorescence detection takes place with the aid of an optics, which contains a narrow-band yellow filter, through which the clear red fluorescence can be identified with the eye. A clear fluorescence of the visible tumor of the urinary bladder appears, which was also clearly visible under white light inspection. In addition 2 smaller, clearly fluorescence positive areas appeared, which had not been identified under white light. It is remarkable, that under the longer irradiation with the blue violet light no bleaching of the fluorescence occurred.

A further examination approach is the fluorescence cytology. In cytology the urine of the patient is tested for malignant cells to find out, if the patient possibly has a bladder tumor relapse. The poorly differentiated bladder tumors can be identified very well by conventional urine cytology. But unfortunately it is difficult to differentiate the cells of the well differentiated bladder carcinoma from the normal urothelia cytologically. However since the well differentiated bladder tumors are also fluorescence positive (the cases described above concern well differentiated bladder tumors), the existence of a bladder tumor can be diagnosed by means of the fluorescence of the excreted cells.

In addition to the precise localisation of the tumors the therapeutical intervention by photodynamic therapy also can be carried out in succession. The tumor (or the lesion as the case may be), which has concentrated the photosensitizer, can in this way be necrotized with appropriate stimulation light and application of energy.

LITERATURE

[1] DOUGHERTY T. J., MARCUS S. L., Photodynamic Therapy. Eur J Cancer, 28 (1992) 1734-1742
[2] HILLEGERSBERG R., KORT W. J., WILSON J. H. P., Current Status of Photodynamic Therapy in Oncology. Drugs, 48 (1994) 510-527
[3] SROKA R., In-vivo Untersuchung Modifizierter Photosensibilisatoren und Entwicklung von Lichtapplikationssystemen für die PDT. Akademischer Verlag München, 1992
[4] BHATTA N., ISAACSON K., BHATTA K. M., ANDERSON R. R., SCHIFF I., Comparative study of different laser systems Fertility and Sterility, 1994, 61, 4; 581-591
[5] BOCK G., HARNETT S., Photosensitizing Compounds: Their Chemistry, Biology and Clinical Use. Ciba Foundation Symposium 146 John Wiley & Sons, 1989
[6] HENDERSON B. W., DOUGHERTY T. J. How does photodynamic therapy work Photochem. Photobiol. 55 (1992) 145-157
[7] KUBIN A., ALTH G., JINDRA R., JESSNER G., EBERMANN R. Wavelength dependent photoresponse of biological and aqueous model systems using the photodynamic plant pigment hypericin. J. Photochem. Photobiol. B: Biology 36 (1996) 103-108
[8] THOMAS C., PARDINI R. S. Oxygen Dependence of Hypericin.induced Phototoxicity to EMT6 Mouse Mammary Carcinoma Cells Photochemistry Photobiology, Vol. 55, No. 6, pp. 831-837, 1992
[9] KNOX J. P., DODGE A. D. Isolation and activity of the photodynamic pigment hypericin Plant, Cell and Environment 8 (1985), 19-25
[10] DURAN N., SONG P. S., Hypericin and its Photodynamic action, Photochemistry and Photobiology, Yearly Review, Vol. 43, No. 6, pp. 677-680, 1986
[11] VANDENBOGAERDE A L., CUVEELE J F., PROOT P., HIMPENS B E., MERLEVEDE W J., deWITTE P A. Differential cytotoxic effects induced after photosensitization by hypericin. J Photochem. Photobiol. B: Biology 38 (1997) 136-142
[12] KNOX J P., DODGE A D. Isolation and activity of the photodynamic pigment hypericin Plant Cell and Environment 8 (1985) 19-25
[13] ANDREONI A., COLASANTI A., COLASANTI P., MASTROCINQUE M., RICCIO P., ROBERTI G. Laser photosensitization of cells by hypericin Photochem. Photobiol. 59 (1994) 529-533
[14] DIWU Z. Novel therapeutic and diagnostic applications of hypocrellins and hypericins Photochem. Photobiol. 61 (1995) 529-539

FURTHER LITERATURE

[15] HESSE M., MEIER H., ZEEH B., Spektroskopische Methoden in der organischen Chemie, G. Thieme Vlg. Stuttgart N.Y. 1984, pp. 1-32.
[16] ELSTNER E. F, Der Sauerstoff Wissenschaftsverlag Mannheim, Wien, Zürich 1990, Band I
[17] YOUNG S. W., QING F., et al. Gadolinium(III)texaphyrin: A tumor selective radiation sensitizer that is detectable by MRI. Proc. Natl. Acad. Sci. USA, 93 (1996) pp. 6610-6615
[18] NITZAN Y, GUTTERMAN M, MALIK Z, EHRENBERG B. Inactivation of Gram-negative bacteria by photosensitized porphyrins. Photochem. Photobiol. 55, 1992, 89-96
[19] HILL J. S., KAHL S. B., STYLLI S. S., NAKAMURA Y., KOO M. S., KAYE A. H., Selective tumor kill of cerebral glioma by photodynamic therapy using a boronated porphyrin photosensitizer. Proc. Natl. Acad. Sci. USA 92 (1995) 12126-12130
[20] SZEIMIES R. M., CALZAVARA PINTON P G., KARRER S., ORTEL B., LANDTHALER M. Topical photodynamic therapy in dermatology. J. Photochem. Photobiol. B: Biology 36 (1996) 213-219
[21] PENG Q., WARLOE T., et al. Distribution of 5-Aminolevulinic acid-induced Porphyrins in nodulouceretive basal cell carcinoma. Photochem. Photobiol. 62 (1995) 906-913
[22] BRAICHOTTE D., SAVARY J F., GLANZMANN T., WESTERMANN P., FOLLI S., WAGNIERES G., MONNIER P., VAN DEN BERGH H., Clinical pharmacokinetic studies of tetra(metahydroxyphenyl)chlorin in squamous cell carcinoma by fluorescence spectroscopy at 2 wavelengths. Int. J. Cancer 63 (1995) 198-204
[23] SUSLICK K S. Die chemische Wirkung von Ultraschall Spektrum der Wissenschaften, 4(1989) 60-66

The invention claimed is:

1. A composition comprising a water-soluble complex of hypericin and a polyvinylpyrrolidone having a molecular weight from 10,000 to 90,000 g/mol in an aqueous solution, wherein the hypericin is a synthetic hypericin or an isolated hypericin.

2. The composition of claim 1, wherein the molecular weight is from 10,000 to 40,000 g/mol.

3. The composition of claim 1, wherein the molar ratio of hypericin to polyvinylpyrrolidone is about 1:1.

4. The composition of claim 1, wherein the concentration of hypericin and the concentration of polyvinylpyrrolidone are both from 1 µmol/l to 0.1 mol/l.

5. A composition comprising a water-soluble complex of a synthetic or isolated hypericin and a polyvinylpyrrolidone having a molecular weight from 10,000 to 90,000 g/mol in an aqueous solution, wherein the concentration of hypericin and the concentration of polyvinylpyrrolidone are both from 1 µmol/l to 0.1 mol/l.

* * * * *